United States Patent

Cheema

[11] Patent Number: 5,509,298
[45] Date of Patent: Apr. 23, 1996

[54] APPARATUS AND METHOD FOR MEASURING VISCO-ELASTIC CHARACTERISTICS OF A SAMPLE

[76] Inventor: Mandranjan S. Cheema, 134 Moorsholm Drive, Nottingham, NG8 2EE, United Kingdom

[21] Appl. No.: 687,880

[22] PCT Filed: Oct. 3, 1989

[86] PCT No.: PCT/GB89/01173

§ 371 Date: Jun. 3, 1991

§ 102(e) Date: Jun. 3, 1991

[87] PCT Pub. No.: WO91/05235

PCT Pub. Date: Apr. 18, 1991

[51] Int. Cl.$^6$ .................................................. G01N 11/00
[52] U.S. Cl. .................... 73/54.41; 73/54.39; 73/815; 73/846
[58] Field of Search .................................. 73/54, 58, 60, 73/841, 846, 815

[56] References Cited

U.S. PATENT DOCUMENTS

| 2,865,197 | 12/1958 | Penther et al. | 73/58 |
| 3,194,064 | 7/1965 | Miles | 73/815 X |
| 4,166,381 | 9/1979 | Woo | 73/54 |

FOREIGN PATENT DOCUMENTS

| 65-136 | 5/1980 | Japan | 73/60 |
| 160045 | 10/1982 | Japan | 73/60 |
| 913165 | 3/1982 | U.S.S.R. | 73/54 |
| 1376104 | 9/1970 | United Kingdom. | |
| 1365677 | 9/1974 | United Kingdom. | |

OTHER PUBLICATIONS

Raha, S. *An Apparatus to measure the dynamic viscoelasticity of Polymer melts.* In. Journ. of Sci. Instr., Series 2, vol. 1, 1968 pp. 1109–1112.

Fruh, S. M., et al. *Recoverable Shear Measurements in a Parallel Plate Rheometer.* In AiChE Jour., vol. 16, No. 6, pp. 907–910, Nov. 1970.

*Dynamic (Oscillatory)Measurements Without Sample Inertia Effects,* Ferry, J. D., Visoelastic Properties of Polymers, Wiley, 1970.

*Sinusoidal Shear Generator for Study of Viscoelasticity,* Miles, D. O., Journal of Applied Physics, vol. 33, No. 4, 1962.

Primary Examiner—Hezron E. Williams
Assistant Examiner—Joseph W. Roskos
Attorney, Agent, or Firm—Lorusso & Loud

[57] ABSTRACT

Apparatus for measuring the fluid characteristics of a sample comprises a frame, at least a first stage mounted on the frame for rectilinear movement, first mounting means mounted on the first stage, and a first member carried by the mounting means, a second member mounted to the frame in register with the first member, at least one of the first member and second member being readily interchangeable, positioning means for moving the first stage to adjust the relative positions of the members whereby a sample carried by one of the members can be brought into contact with the other of the members and whereby to adjust the spacing between the first and second members to a preselected distance, a device for vibrating the first mounting means rectilinearly, and thus the first member carried thereby, at a preselected frequency. A Piezo-electric device is provided for vibrating the first member rectilinearly as indicated by the arrow and a force transducer detects the phase angle and amplitude of the vibration transmitted through the sample. Relationship between the vibration applied by the device and those received by the transducer are used by a controlling computer to calculate the characteristics of the sample. The apparatus can operate over a wide range of frequencies; the sample temperature can be accurately controlled.

36 Claims, 2 Drawing Sheets

APPARATUS AND METHOD FOR MEASURING VISCO-ELASTIC CHARACTERISTICS OF A SAMPLE

This invention is concerned with an apparatus and method suitable for use in measuring the characteristics of a sample, especially the flow characteristics of liquid or semi-solid materials, for example printing inks, greases, oils and the like.

In assessing the suitability of various materials for particular functions it is important to know the characteristics of the materials under a variety of conditions. To this end it has been proposed to subject samples of materials to be assessed to intermittent distorting forces to provide data relating to their liquid/solid behaviour. However, existing apparatus for determining the characteristics of such material samples have not been altogether satisfactory. Suitable known equipment has in many cases only been capable of operating at frequencies of up to 15 Hz. and whilst this has provided some useful data, the frequency is too low to give fully satisfactory data for many purposes—for example, an engine rotating at 6000 rpm is rotating at a frequency of 100 Hz. and it would therefore be useful to be readily able to test the characteristics of oils at frequencies at least up to this level. Known apparatus for measuring the characteristics of samples has consisted of two plates between which a sample to be tested is positioned in contact with both plates, one of the plates being oscillated or rotated around an axis perpendicular to the other plate (which is generally fixed) to measure torsional shear characteristics. The rotation of the plates round the axis does not give sufficiently revealing data in most instances, and commonly known apparatus in which the plate is oscillated has not been capable of oscillating at a frequency significantly in excess of 15 Hz because the mass (and therefore inertia) of the equipment necessary to achieve such an oscillation has restricted the frequency. One such known apparatus may use a relatively large electric motor including a shaft mounted on an armature, to which alternating current is applied at a suitable frequency thus to oscillate the shaft about its axis: such an oscillation is relatively free and uncontrolled and it is difficult to achieve very precise measurements at high frequencies using such apparatus. In this equipment the forces may be determined via the oscillating shaft or the fixed plate. In another known apparatus, the oscillation is effected using a mechanical linkage which provides a more precise control of the amplitude of oscillation but is relatively complex and still has limitations of frequency due to the inertia of the various parts. In such apparatus the force applied through the sample may be detected by means of a transducer in a support member by which the sample is supported. One apparatus of this general oscillating type, using a mechanically operated member, is described in patent GB-A-1365677.

One of the various objects of the present invention is to provide an improved apparatus suitable for use in measuring the characteristics of a sample.

In one aspect the invention may be considered to provide apparatus suitable for use in measuring the visco-elastic characteristics of a sample comprising a support member providing a flat support surface on which the sample may be positioned, a cover member providing a flat surface, means for adjusting the relative positions of the members whereby to bring a sample carried by the support surface into contact with the flat surface of the cover member and to adjust the spacing between the flat surfaces to a preselected distance, means for vibrating one of the members at one or more preselected frequencies, and means for detecting the behaviour of the sample. Said means for vibrating one of the members may vibrate the member at a single preselected frequency, or at a certain number of preselected frequencies simultaneously, for example two or preferably three or even more.

Preferably vibrating means of apparatus in accordance with the invention comprise a form of electrically driven oscillator for example a piezo-electric device; said vibrating means is preferably adapted to vibrate said one of the members rectilinearly. Preferably the apparatus comprises means for adjusting both the amplitude and frequency of vibration, from a very low frequency (almost zero) to a much higher frequency, conveniently between about 0.001 Hz and 2000 Hz.

In a preferred apparatus in accordance with the invention the vibrating means is adapted to vibrate the support member and the detecting means is associated with the cover member and adapted to detect forces transmitted to the cover member through the sample. In this apparatus the temperature control means for the sample comprises a temperature control member disposed below but spaced slightly from the support member and a small volume of heat transfer fluid is positioned between the support member and temperature control member whereby to rapidly transfer heat to and from the support member.

In another apparatus in accordance with the invention the support member is fixed and the vibrating means is adapted to vibrate the cover member, detecting means being associated with the cover member and adapted to detect the force applied through the cover member. In this instance, the support member comprises temperature control means by which the temperature of the support member can be controlled whereby to control the temperature of the sample.

In another aspect the invention may be considered to provide a method of measuring visco-elastic characteristics of a sample comprising placing a sample on a flat support surface of a support member, moving a cover member towards the surface into engagement with the sample until a flat surface of the cover member engaging the sample is spaced a preselected distance from the support surface, causing one of the members to vibrate by means of an electrical oscillator through a small amplitude relative to the other member and at a controlled frequency, detecting the force applied to the sample, and relating the detected force applied to the vibration of the oscillator whereby to determine the properties of the sample.

Preferably in a preferred method in accordance with the invention the phase lag and amplitude, detected relative to the phase and amplitude of the applied vibration, are used to determine the properties of the sample according to various mathematical calculations which are known to those skilled in the art. In carrying out a method in accordance with the invention apparatus in accordance with the invention is preferably used. Normally in a method in accordance with the invention the vibration will not exceed 2000 Hz and preferably lies between 1 Hz and 1500 Hz, more preferably between 5 Hz and 1200 Hz.

There now follows a detailed description to be read with reference to the accompanying drawings of apparatus embodying the invention. It will be realised that this apparatus has been selected for description to illustrate the invention by way of example.

Figure 1:
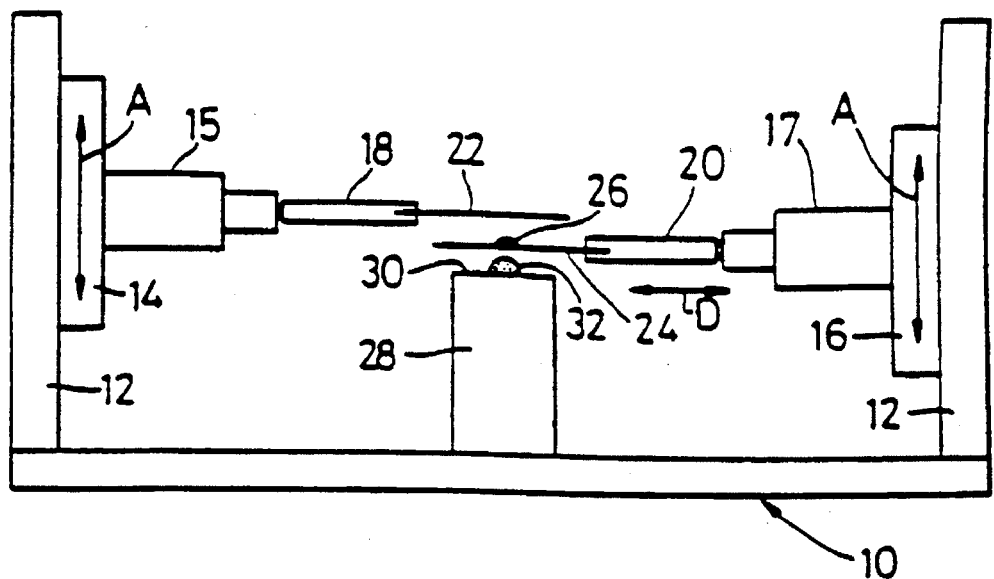
FIG. 1 is a diagrammatic front view of apparatus in accordance with the invention as the apparatus is being set up.
Figure 2:
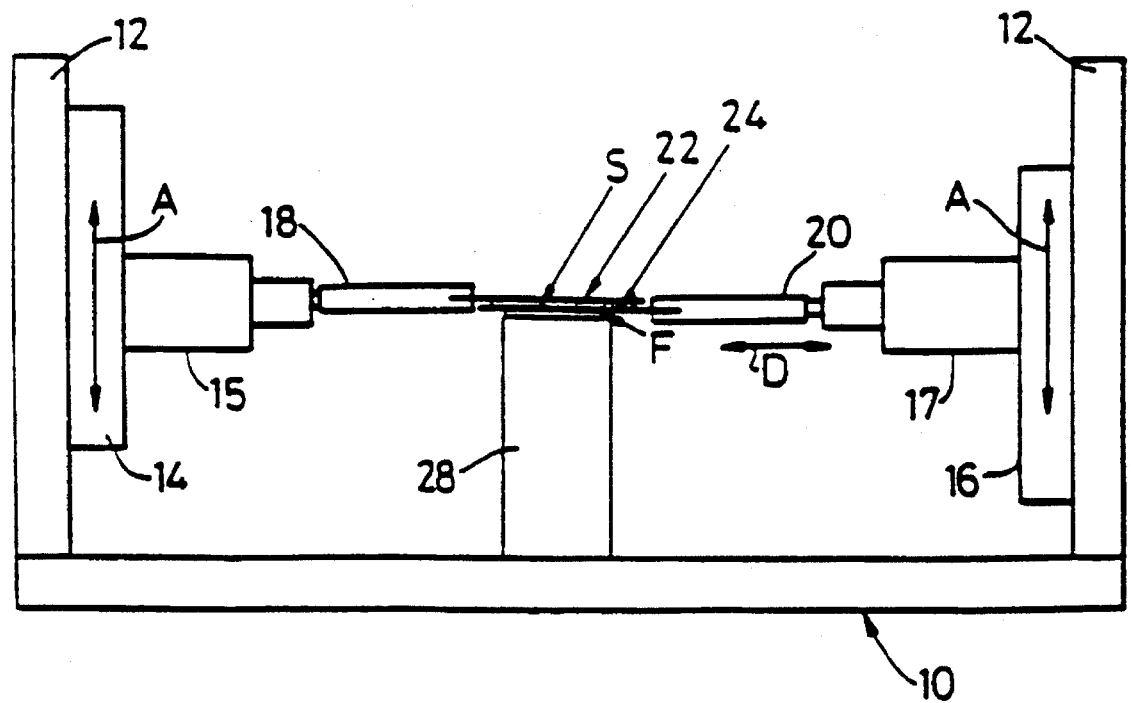
FIG. 2 is a view similar to FIG. 1 showing the apparatus in operation.

The illustrative apparatus comprises frame means 10 comprising pillars 12 at opposite sides of the frame means. On each of the pillars 12 a stage 14, 16 is mounted for up and down movement as indicated by the arrows A. Mounted on the stages 14, 16 respectively are beams 18, 20 which are extremely light and carry at their inner end portions flat plates 22, 24 which lie horizontally. A lower one of the plates 24 provides a support member for a sample 26 whilst the upper plate 22 provides a cover member. As can be seen viewing FIGS. 1 and 2 the plates 22, 24 are positioned when the apparatus is operative in register with one another. The plates 22, 24 may be made of any suitable material, for example polymeric material or glass, provided that the surface is flat and of sufficient hardness.

Positioning means (not shown) is mounted on the pillars 12 for moving the stages 14, 16 upwardly and downwardly in the direction indicated by the arrows A. The positioning means may comprise any known means for moving apparatus accurately, for example precision slideways for guiding the stages 14, 16 and a lead screw driven by a stepper motor in engagement with a nut carried by the stage whereby to accurately position the stages relative to one another. Alternatively, a rolex mechanism together with optical locating means may be used. Other positioning means may also be used if desired.

The illustrative apparatus further comprises temperature control means comprising a temperature control member provided by a block 28 carried by the frame 10. Block 28 has a flat upper surface 30 which is in register with the plates 22, 24 when they are in their operative positions. The upper surface 30 is positioned below the lower plate 24. Means is provided in the block 28 for controlling the temperature of the block 28 and may include heating means and cooling means, if desired.

Mounted on the stage 16 is vibrating means comprising a piezo-electric device 17 which is adapted to vibrate the plate 24, through the beam 20, recti-linearly in the direction indicated by the arrow D. Mounted on the stage 14 is a detecting means comprising a force transducer 15 of known construction and which is sensitive to very small forces. The beams 18, 20 and plates 22, 24 are very light, and thus the piezo-electric device 17 is able to reciprocate the plate 24 at a very high frequency in the direction indicated by the arrow D, up to about 2000 Hz, as the inertia of the beam 20 and plate 24 combination is very low. Likewise the inertia of the beam 18/plate 22 combination is very low and thus the transducer 15 is very sensitive to the transmitted vibrations.

The illustrative apparatus also comprises computer means by which the illustrative apparatus is controlled during operation and to which the output from the fourth transducer associated with the beam 18 and plate 22 is supplied.

In the operation of the illustrative apparatus, the two stages 14, 16 are initially in their fully raised positions, that of the stage 14 being higher than that of the stage 16. Fresh plates 22, 24 are clamped to the beams 18, 20 by suitable clamp means (not shown). If desired means may be provided whereby the beams may be pivoted to positions lying substantially at right angles to the direction indicated by the arrow D and the arrows A to facilitate access.

A sample of material to be tested is positioned on the flat surface of the lower plate 24 which provides a support surface. The sample 26 may be very small, smaller than has been possible with many previously known devices for measuring characteristics of samples. Also, at the same time a drop 32 of small volume, for example about 0.01 millilitres, of a suitable heat transfer fluid is placed on the upper surface 30 of the block 28. The stage 16 is then lowered, by the computer, to a position in which the lower surface of the plate 24 is spaced slightly from the upper surface 30 of the block, the drop 32 thus being caused to spread and form a film between the plate 24 and the surface 30 as indicated at the arrow F in FIG. 2. The stage 14 is also then caused to descend from its raised position by the computer until the lower surface of the plate 22 is spaced a preselected distance above the upper surface of the plate 24. The spacing between the plates, 22, 24 is selected according to the sample S which is to be tested. As can be seen viewing FIG. 2, the sample S spreads to form a film between the plates 22, 24. The temperature control means is activated to adjust the temperature of the block 28 to a desired temperature which is readily transmitted through the heat transfer fluid F and the thin plate 24 to the sample S. As the fluid F and plate 24 are very insubstantial, the temperature of the sample S can be controlled via the block 28 very accurately. When the sample S has reached the desired temperature, the piezo-electric device 17 is started by the computer to vibrate at a preselected frequency and amplitude, dependent upon the sample to be tested, thus to vibrate the plate 24 rectilinearly and a signal is detected by the force transducer 15 carried by the stage 14. The output from the force transducer 15 is fed to the computer and compared with the signal provided by the piezo-electric device 17 which is likewise under the control of the computer. The computer is thus able to determine both the phase lag detected by the force transducer and the ratio between the amplitude of the signal provided by the piezo-electric device (which is applied via the lower plate 24 to the sample) and the amplitude of the output signal from the force transducer which is obtained by the movement of the upper plate 22 through the sample S.

Using the programme included in the computer software, which utilises known mathematical calculations, the phase angle $\theta$ is calculated from the amplitude ratio and the phase lag and the flow properties of the sample are indicated by tan $\delta$, G' and G". Tan $\delta = G'/G''$, that is the ratio of the viscous to the elastic modulus. This is a measurement which has gained widespread importance, especially in polymer rheology. In carrying out the illustrative method the sample is subjected to a shearing motion. The relative movement between the two plates 22, 24 depends on the visco-elasticity of the sample. In order to provide data which is useful it is desirable to ensure that the sample is in a condition in which the mathematical formula used to calculate the characteristics are substantially linear: this occurs when the shear angle is very small e.g. less than 0.01 radians. Thus the spacing between the plates 22, 24 must be chosen to ensure that with the sample in question, this shear angle is not exceeded. However, in some circumstances it may be desired to investigate the region in which the mathematical relationships are no longer linear and in this event shear angle of more than 0.01 radians may be appropriate. Non-linear effects occur when the sample is stretched irreversibly, that is it does not revert to its original state after removal of stress.

The concepts on which the mathematical treatment of the results is based are discussed in the book "Rheometry" by Professor K. Walters published in 1975 by Chapman & Hall, London, ISBN 0 412 120909. Reference is directed particularly to pages 120 to 209, especially pages 133 to 160.

In order to provide the necessary control, the means for moving the stages 14, 16 must be capable of positioning the beams 18, 20 to an accuracy of $\pm 1 \times 10^{-6}$ m.

The computer can be controlled to investigate the sample S at a variety of different frequencies and amplitudes, and the temperature control means is also under the control of the computer so this can readily be varied also.

The illustrative apparatus is easier to use than the various previously proposed oscillatory apparatuses referred to above which are commonly used; for example it is simpler to load and unload the samples. Furthermore the apparatus is easier to clean and the plates 22, 24 may be disposed of after having been used once and replaced by new plates as these are relatively cheap if made from glass. As previously mentioned a greater frequency range can be explored than has heretofore been possible. Furthermore, the construction of the apparatus is relatively simple and the apparatus is thus expected to be less expensive than known apparatus.

As will be appreciated, the illustrative apparatus is susceptible to external vibration and thus is desirably mounted on an anti-vibration table.

Furthermore, because the vibration is produced by a piezo-electric device under the control of the computer, and the detecting means is a force transducer also connected with the controlling computer, the results of the measurements can be computed rapidly within the illustrative apparatus. The illustrative apparatus preferably is controlled directly from the computer using a so-called "mouse": using a preferred computer a "control panel" for the illustrative apparatus may be simulated on the video screen of the computer and operated by the "mouse", using commercially available software to operate the illustrative apparatus.

Two alternative apparatuses embodying the invention are also described hereinafter. In the descriptions of these alternative apparatuses like numbers indicate like parts.

Figure 3:
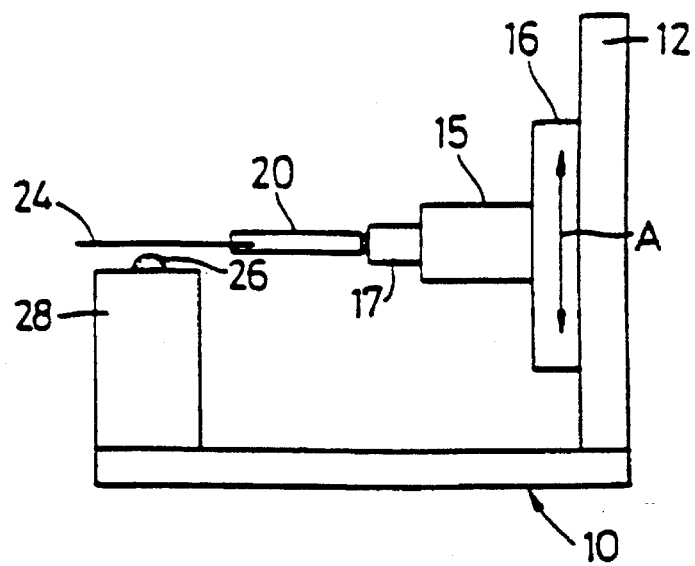
FIG. 3 is a view similar to FIG. 1 showing a first alternative apparatus embodying the invention.

In a first alternative apparatus embodying the invention (see FIG. 3), the stage 14 and ancillary equipment may be omitted and the sample 26 to be tested may be placed directly on the flat upper surface of the temperature control block 28 (in place of the temperature control fluid 32). The detecting means in this instance, will be associated with the beam 20 so that the piezo-electric device 17 and the force transducer 15 of the detecting means will be carried by the same stage 16 (as shown in FIG. 3). In this first modified apparatus, the sample 26 can be heated directly by the temperature control block 28. Similar software may be used to calculate the characteristics of the sample though the software may need to be modified in view of the mounting of the force transducer in association with the beam 20. However, the use of only a single stage and associated accurate positioning means may considerably reduce the cost and increase ease of use of the first modified illustrative apparatus.

Figure 4:
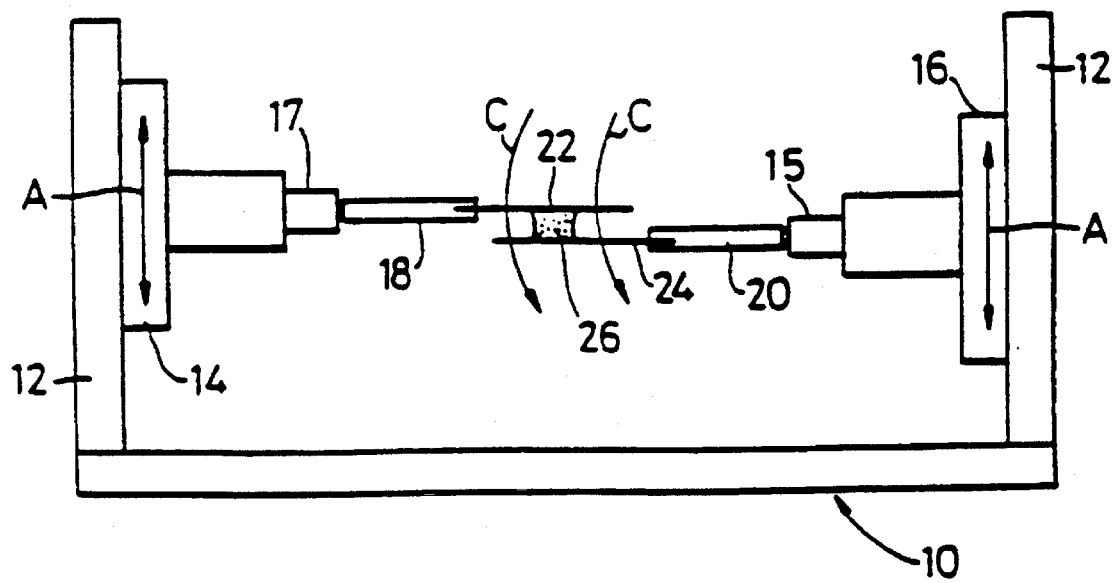
FIG. 4 is a view generally similar to FIG. 1 showing a second alternative apparatus embodying the invention.

A second alternative apparatus is shown in FIG. 4 and in this apparatus the sample 26 may be heated by a circulating fluid (as indicated by the arrows C), namely an appropriate gas. Air of controlled humidity may be used for this purpose.

It should be noted that inertial effects are unavoidable in low viscosity systems at high frequencies. The sample geometry in the invention is especially suited to mathematical treatment of this problem.

Problems can occur near to the resonant frequency (or multiples thereof) of the apparatus: these can be minimised by designing beams 18, 20 specially adapted for use in specific frequency ranges.

I claim:

1. Apparatus suitable for use in measuring the visco-elastic characteristics of a sample comprising frame means, at least a first stage mounted on said frame means for rectilinear movement, first mounting means mounted on said first stage, and a first member carried by said mounting means, a second member mounted to said frame means in register with said first member, at least one of the first member and second member being readily interchangeable, positioning means for moving the first stage to adjust the relative positions of said members whereby a sample carried by one of said members can be brought into contact with the other of said members and whereby to adjust the spacing between the first and second members to a preselected distance, means for vibrating said first mounting means rectilinearly, and thus said first member carried thereby, at a preselected frequency, and means for detecting the behaviour of said sample.

2. Apparatus according to claim 1 wherein said means for vibrating said first mounting means comprises a piezo-electric device.

3. Apparatus according to claim 1 comprising means for adjusting the frequency of vibration.

4. Apparatus according to claim 3 wherein the frequency can be adjusted between 0.001 Hz and 2000 Hz.

5. Apparatus according to claim 1 comprising means for adjusting the amplitude of vibration.

6. Apparatus according to claim 1 wherein said detecting means is adapted to detect movement of said second member transmitted through said sample.

7. Apparatus according to claim 6 comprising a temperature control member said first member being disposed above but spaced slightly from said temperature control member.

8. Apparatus according to claim 1 wherein said second member is fixed and said vibrating means is adapted to vibrate said first member, said detecting means being associated with said first member and adapted to detect force applied to the sample.

9. Apparatus according to claim 8 wherein said second member comprises temperature control means by which the temperature of said second member can be controlled to control the temperature of said sample.

10. Apparatus according to claim 1 wherein the detecting means comprises a force transducer.

11. Apparatus according to claim 1 wherein the second member is carried by a second mounting means carried by the frame means and the detecting means is associated with the second mounting means.

12. Apparatus according to claim 11 comprising a second stage mounted on the frame means for rectilinear movement, the second mounting means being mounted on the second stage.

13. Apparatus according to claim 12 comprising positioning means for moving the second stage, whereby the relative positions of said members can be adjusted by movement of both first and second stages.

14. Apparatus according to claim 12 wherein said sample is carried by said first member.

15. Apparatus according to claim 14 comprising a temperature control member, said first member being disposed above but spaced slightly from said temperature control member, heat transfer fluid being arranged to be positioned between said first member and said temperature control member whereby to transfer heat to or from said first member.

16. Apparatus according to claim 1 wherein said means for detecting the behaviour of the sample is associated with the first mounting means.

17. A method of measuring visco-elastic characteristics of a sample comprising placing a sample on a first member or second member of an apparatus comprising a frame means, said frame means comprising at least a first stage mounted on said frame means for rectilinear movement, first mounting means mounted on said first stage and a first member carried by said mounting means, said second member mounted to said frame means in register with said first member, moving said first member to adjust the relative positions of said members until said first member is spaced a preselected distance from said second member whereby said sample can be brought into contact with said other member causing said first member to vibrate rectilinearly by means of an electrical oscillator through a small amplitude relative to said second member and at a controlled frequency, detecting the force applied to the sample, and relating the detected force applied to the vibration of the oscillator whereby to determine the properties of the sample.

18. A method according to claim 17 wherein the phase lag and amplitude detected relative to the applied vibration are used to determine the properties.

19. A method according to claim 17 wherein the vibration is applied to said first member by means of a piezo-electric device.

20. A method according to claim 17 wherein said detecting means is adapted to detect movement of said first member transmitted through said sample.

21. A method according to claim 17 wherein said second member is fixed, and reaction force is detected through said first member.

22. A method according to claim 17 wherein said sample is excited at more than one frequency.

23. A method according to claim 17 wherein the temperature of said sample is controlled.

24. A method according to claim 17 wherein said frequency of vibration does not exceed 2000 Hz.

25. A method according to claim 17 wherein said frequency of vibration lies between 1 Hz and 1500 Hz.

26. A method according to claim 17 wherein said frequency lies between 5 Hz and 1000 Hz.

27. Method according to claim 17 wherein in said detecting step said force applied to said sample is detected by movement of said second member transmitted through said sample.

28. Method according to claim 27 including the step of heating said sample by means of a temperature control member, said first member being disposed above said temperature control member.

29. Method according to claim 17 wherein in said step of placing said sample said second member is fixed and in said detecting step said force applied to said sample is detected by movement of said first member transmitted through said sample.

30. Method according to claim 29 including the step of heating said sample comprising a temperature control means by which the temperature of said second member can be controlled to control the temperature of said sample, 31. Method according to claim 17 wherein in said placing step said second member is carried by a second mounting means carried by said frame means and in said detecting step said force applied to said sample is detected by movement of said second mounting means transmitted through said sample, 32. Method according to claim 31 wherein in said placing step a second stage mounted on said frame means for rectilinear movement is provided, said second mounting means being mounted on said second stage.

33. Method according to claim 32 wherein in said moving step the relative positions of said member can be adjusted by movement of both said first and second stages, 34. Method according to claim 32 wherein in said placing step said sample is placed on said first member.

35. Method according to claim 34 including the step of heating said sample comprising a temperature control member, said first member being disposed above said temperature control member, heat transfer fluid being arranged to be positioned between said first member and said temperature control member whereby to transfer heat to or from said first member.

36. Method according to claim 17 wherein in said detecting step said force applied to said sample is detected by movement of said first mounting means transmitted through said sample.

* * * * *